(12) United States Patent
Charkhandeh

(10) Patent No.: US 10,751,153 B2
(45) Date of Patent: Aug. 25, 2020

(54) APPARATUS AND METHOD FOR REGISTRATION OF A DIGITAL DENTAL BITE

(71) Applicant: ZST Holdings, Inc., Calgary (CA)

(72) Inventor: Shouresh Charkhandeh, Edmonton (CA)

(73) Assignee: ZST HOLDINGS, INC., Calgary, AB (CA)

( * ) Notice: Subject to any disclaimer, the term of this patent is extended or adjusted under 35 U.S.C. 154(b) by 0 days.

(21) Appl. No.: 16/185,529

(22) Filed: Nov. 9, 2018

(65) Prior Publication Data

US 2019/0076227 A1 Mar. 14, 2019

Related U.S. Application Data

(63) Continuation of application No. PCT/IB2018/056654, filed on Aug. 30, 2018.

(60) Provisional application No. 62/551,851, filed on Aug. 30, 2017.

(51) Int. Cl.
| | |
|---|---|
| *A61C 19/05* | (2006.01) |
| *A61C 9/00* | (2006.01) |
| *A61B 13/00* | (2006.01) |
| *A61B 5/00* | (2006.01) |
| *A61F 5/56* | (2006.01) |

(52) U.S. Cl.
CPC ............ *A61C 19/05* (2013.01); *A61B 5/4818* (2013.01); *A61B 13/00* (2013.01); *A61C 9/0006* (2013.01); *A61C 9/0046* (2013.01); *A61F 5/566* (2013.01)

(58) Field of Classification Search
CPC ..... A61C 19/05; A61C 9/0006; A61C 9/0046; A61C 19/06; A61B 5/4818; A61F 5/566

USPC .......................................... 433/37–38, 68–69
See application file for complete search history.

(56) References Cited

U.S. PATENT DOCUMENTS

| 1,611,201 | A | * | 12/1926 | Kidder | ................ | A61C 9/0006 |
| | | | | | | 433/45 |
| 2,597,929 | A | * | 5/1952 | Gorsky | ................ | A61C 9/0006 |
| | | | | | | 433/37 |
| 3,532,091 | A | * | 10/1970 | Lerman | ................ | A63B 71/085 |
| | | | | | | 128/861 |
| 4,211,008 | A | | 7/1980 | Lerman | | |

(Continued)

FOREIGN PATENT DOCUMENTS

| DE | 102015206490 | 10/2016 |
| WO | 2010/141220 | 12/2010 |

(Continued)

OTHER PUBLICATIONS

Airway Metrics Webpage (Year: 2018).*

(Continued)

*Primary Examiner* — Yogesh P Patel
(74) *Attorney, Agent, or Firm* — Meunier Carlin & Curfman LLC

(57) ABSTRACT

An example apparatus for use in obtaining digital open bite registration is described herein. The apparatus can include a bite fork configured to fit in a subject's mouth. The bite fork can include at least one molar pad and at least one incisor pad, each of the at least one molar pad and the at least one incisor pad having respective upper and lower bite surfaces. The apparatus can further include a lingual band extending between the at least one molar pad and the at least one incisor pad.

24 Claims, 5 Drawing Sheets

(56) References Cited

U.S. PATENT DOCUMENTS

| | | | |
|---|---|---|---|
| 5,059,120 A * | 10/1991 | Lee | A61C 9/0006 |
| | | | 433/37 |
| 5,154,609 A | 10/1992 | George | |
| 7,697,968 B2 | 4/2010 | Moore | |
| 8,453,650 B1 | 6/2013 | Frey | |
| 8,684,006 B2 | 4/2014 | Levendowski et al. | |
| 2006/0201520 A1 * | 9/2006 | Christensen, III | A61C 9/0006 |
| | | | 128/848 |
| 2010/0300457 A1 | 12/2010 | Horchover | |
| 2011/0059413 A1 | 3/2011 | Schutyser et al. | |
| 2015/0118640 A1 | 4/2015 | Schmitt | |
| 2015/0164682 A1 * | 6/2015 | Remmers | A61B 5/4812 |
| | | | 600/301 |
| 2016/0008107 A1 | 1/2016 | Brunner | |
| 2016/0220340 A1 * | 8/2016 | Carrillo Gonzalez | |
| | | | A61C 19/05 |

FOREIGN PATENT DOCUMENTS

| | | |
|---|---|---|
| WO | 2013/188660 | 12/2013 |
| WO | 2014/159236 | 10/2014 |

OTHER PUBLICATIONS

Charkhandeh et al. "A Fully Digital Workflow and Device Manufacturing for Mandibular Repositioning Devices for the Treatment of Obstructive Sleep Apnea; A Feasibility Study," Journal of Dental Sleep Medicine. 2017;4(4):97-102.
Airway Metrics Webpage, accessed Aug. 29, 2018, 2 pages.
International Search Report and Written Opinion received in International Application No. PCT/IB2018/056654 dated Dec. 17, 2018, 10 pages.

\* cited by examiner

APPARATUS AND METHOD FOR REGISTRATION OF A DIGITAL DENTAL BITE

CROSS-REFERENCE TO RELATED APPLICATIONS

This application is a continuation of International patent application No. PCT/IB2018/056654, filed on Aug. 30, 2018, and entitled, "Apparatus and Method for Registration of a Digital Dental Bite," which claims the benefit of U.S. provisional patent application No. 62/551,851, filed on Aug. 30, 2017, and entitled "Apparatus and Method for Registration of a Digital Dental Bite," the disclosures of which are expressly incorporated herein by reference in their entireties.

BACKGROUND

Obstructive Sleep Apnea (OSA) is a very common chronic disease with many adverse clinical consequences, affecting an estimated 10-20% of population. The majority of these patients remain undiagnosed and the studies show the percentage of undiagnosed OSA could be as high as 80-90%. Untreated OSA is associated with higher risk of fatal cardiovascular and cerebrovascular event, hence, the importance of long-term treatment of the patients. Currently, the most common prescribed treatment for OSA patients is continuous positive airway pressure (CPAP) therapy. Although this treatment is very efficacious and relatively safe with minor side-effects, the patient compliance is low and many patients refuse to start treatment on CPAP. It is reported that the compliance could be as low as 50%, therefore an alternative therapy is required. Many patients prefer oral appliance therapy and compliance is reported to be higher than CPAP. There has been a tremendous growth in this area of dentistry over the past decade and many patients are now seeking this treatment modality.

The number of patients seeking oral appliance therapy will increase current clinical workflow models and device manufacturing may not be able to keep up with the increased demand. Therefore, having more efficient workflow systems and device manufacturing becomes crucial in delivery of care. Digital manufacturing of oral appliances is becoming increasingly popular, favored for the cost savings in manufacturing the device as well as the ability to make modifications easily to the patient's custom device. To date, the digitally manufactured devices are generally made from scans of physical models, poured from plaster and made from physical registration of the bite using a typical bite fork (e.g. a GEORGE GAUGE of Great Lakes Orthodontics, Ltd. of Tonawanda, N.Y. and/or as described in U.S. Pat. No. 5,154,609 to George). The use of a physical bite registration in the digital manufacture of devices creates inefficiencies in the workflow, and can also introduce inaccuracies in the device manufacturing as the difference in the degree of accuracy between conventional bite registration using Polyvinyl Siloxane (PVS) material and digital bite registration could result in improper articulation of the models.

SUMMARY

Apparatuses and methods for registration of the digital dental bite of a patient are described herein. An apparatus including a bite fork is provided for insertion into the patient's mouth. The bite fork maintains a set positioning of the upper and lower dentition and allows a digital scan to be collected (e.g., an intra oral digital scan of the patient's dentition). For example, an intra oral scanner can be used to capture digital impressions of the patient's teeth and registration of the maxilla-mandibular occlusal relationship, i.e., bite registration. The apparatus is designed to remain out of a focal point of the digital scanner. Bite registration information can be used to manufacture oral appliances used to treat OSA, or for other purposes where translating and/or capturing a precise occlusion is required. For example, bite registration information can be used in the production of dentures, or to achieve a therapeutic position for the relief of stresses from occluding surfaces or masticatory muscle related stresses.

An example apparatus for use in obtaining digital open bite registration is described herein. The apparatus can include a bite fork configured to fit in a subject's mouth. The bite fork can include at least one molar pad and at least one incisor pad, each of which has respective upper and lower bite surfaces. The apparatus can also include a lingual band extending between the at least one molar pad and the at least one incisor pad.

In addition, the lingual band can be configured to extend proximate to a lingual portion of the subject's teeth. In some implementations, the lingual band can be configured to be restricted to a region that is proximate to the lingual portion of the subject's teeth. Alternatively or additionally, in some implementations, the lingual band can be configured to not interfere with a buccal portion of the subject's teeth. In some implementations, the lingual band can be coplanar with the at least one molar pad and the at least one incisor pad. In other implementations, the lingual band can be shaped to extend towards the gingival edge. For example, the lingual band can be shaped to be offset caudally with respect to a plane of the occlusal contacting surfaces of the subject's teeth. Optionally, the lingual band offset can be configured to extend below at least a portion of the subject's lower teeth. For example, the lingual band offset can be about 5 to 8 mm relative to the bite fork.

Alternatively or additionally, the bite fork can further include a portion configured to extend outside of the subject's mouth. Optionally, the portion extending outside of the subject's mouth includes a connector which is attachable to an external device (e.g., a George Gauge or a mandibular displacement device).

Alternatively or additionally, the lingual band can be positioned out of a focal point of a digital scanner when the bite fork is positioned in the subject's mouth. For example, the digital scanner can be configured to capture a digital image of the subject's open bite, and the digital image can be used to register a position of the subject's mandible relative to the subject's maxilla. Optionally, the lingual band can be configured to retract the subject's tongue.

Alternatively or additionally, the apparatus can further include an incisal notch configured to receive the subject's upper incisors. The incisal notch can be configured to position the subject's upper and lower incisors with a variable amount of vertical opening there between.

Alternatively or additionally, the apparatus can further include an impression material attached to at least one of the bite surfaces of the at least one molar pad or the at least one incisor pad. Optionally, a thickness of the impression material can be selected to provide a predetermined amount of space between the subject's upper and lower teeth. Alternatively or additionally, the impression material can include one or more layers of impression material.

Alternatively or additionally, the apparatus can further include at least two molar pads and a plurality of lingual bands. Each respective lingual band can extend between the at least one incisor pad and one of the at least two molar pads.

Alternatively or additionally, the apparatus can further include an upper molar tray for receiving at least one of the subject's upper molars, and a lower molar tray for receiving at least one of the subject's lower molars. The at least one molar pad can include an upper molar pad having the upper bite surface and a lower molar pad having the lower bite surface. Additionally, the upper and lower molar pads can be arranged on the upper and lower molar trays, respectively.

Alternatively or additionally, the apparatus can further include an upper incisor tray for receiving at least one of the subject's upper incisors, and a lower incisor tray for receiving at least one of the subject's lower incisors. The at least one incisor pad can include an upper incisor pad having the upper bite surface and a lower incisor pad having the lower bite surface. Additionally, the upper and lower incisor pads can be arranged on the upper and lower incisor trays, respectively.

An example method for obtaining digital open bite registration is also described herein. This disclosure contemplates that the apparatus for use in obtaining digital open bite registration as described herein can be used with the method. The method can include placing a bite apparatus in a subject's mouth; capturing, using a digital scanner, a digital image of the subject's open bite with the bite apparatus in the subject's mouth; and analyzing the digital image to register a position of the subject's mandible relative to the subject's maxilla.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
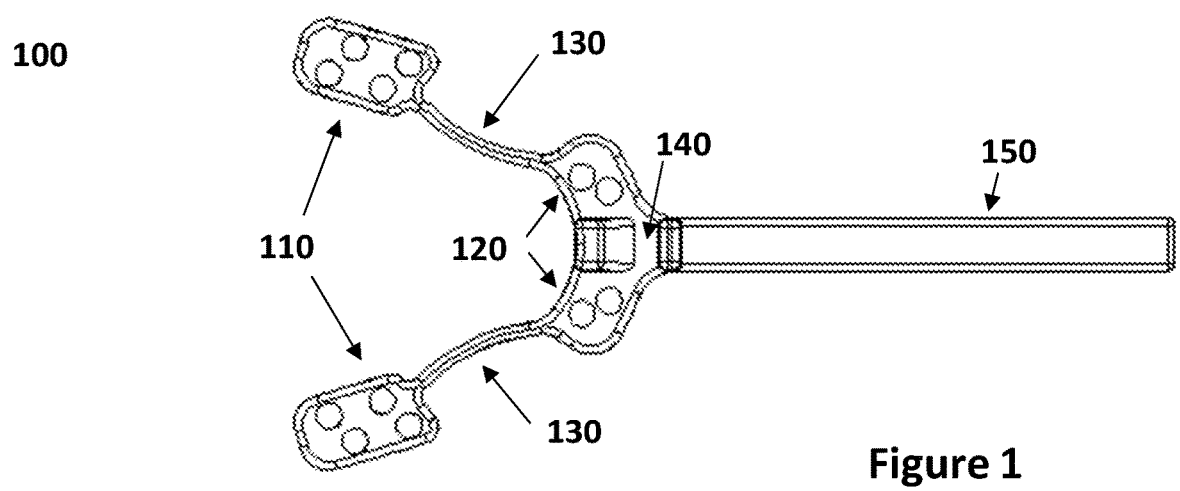
FIG. 1 is a diagram illustrating a top view of an example apparatus for use in obtaining digital bite registration according to implementations described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Digital scanners have been used widely in the dental industry over the past decade, and the accuracy of such scanners is improving. The scanners are able to capture the details of the dentition such that the relative positioning of a subject's (or patient's) maxilla to the subject's mandible can be determined from digital images. This information can be used to produce an oral appliance at the same positioning. However, there are inconsistencies in the bite registration results when the teeth are not fully occluding (sometimes referred to as "Digital Open Bite Registration"). The open bite is required for the purpose of oral appliance manufacturing. For an open bite, if the scans are taken with nothing in the patient's mouth, the quality is poor as the patient is required to hold the desired position for several minutes while the scan is taken, and the clinician has difficulty in precisely positioning the bite. Further, for capturing the precise positioning of a bite, it may be desirable to capture the bite with the device used to determine the appropriate bite position still in the mouth. For example, if a dental tray was used while testing multiple positions of mandible during a test (for example during a sleep test), it may be desirable to capture the bite directly with the same dental tray used during the sleep test. Example methods and apparatuses (including dental trays) for performing titrations for oral appliance therapy are described in detail in WO2013/188660, published Dec. 19, 2013, entitled "Methods and Apparatuses for Performing Remote Titration of Mandibular Protrusion" and WO2014/159236, published Oct. 2, 2014, entitled "Systems and Methods for Providing an Automated Titration for Oral Appliance Therapy." This disclosure contemplates that the apparatuses described herein (e.g., apparatus shown in any one of FIGS. 1-9) can be used as the dental trays described in WO2013/188660 or WO2014/159236. For example, the apparatuses described herein can optionally be attached to a mandibular displacement device via the portion extending outside the subject's mouth. Thus, in some implementations, the apparatuses described herein (e.g., apparatus shown in any one of FIGS. 1-9) can be attached to a mandibular displacement devices that is used to perform the sleep test, and following completion of the sleep test, the same apparatus can be used to obtain the subject's digital open bite registration.

This disclosure also contemplates that the apparatuses described herein (e.g., apparatus shown in any one of FIGS.

1-9) can be used with systems and methods described in WO2010/141220, published Dec. 9, 2010, entitled "Method and apparatus for treating sleep apnea," U.S. Pat. No. 8,684,006 to Levendowski et al., issued Apr. 1, 2014, entitled "Systems and methods for optimizing oral appliance therapy for the treatment of sleep apnea," or U.S. Pat. No. 7,697,968 to Moore, issued Apr. 13, 2010, entitled "System and method of predicting efficacy of tongue-base therapies." Similar to above, the apparatuses described herein can optionally be attached to an external device/component via the portion extending outside the subject's mouth.

This disclosure further contemplates that digital bite registration information can be used in applications other than diagnosing, evaluating, and/or treating sleep apnea. In other words, the apparatuses described herein (e.g., apparatus shown in any one of FIGS. 1-9) can be used with systems and/or methods to produce a denture, to achieve a therapeutic position to relieve stresses from occluding surfaces or masticatory muscle related stress, and/or for other purposes where translating and/or capturing precise occlusion is required. U.S. Pat. No. 4,211,008 to Lerman, issued Jul. 8, 1980, entitled "Oral Device" and DE102015206490B4, issued Oct. 20, 2016 describe other example systems and methods with which the apparatuses described herein may be used. This disclosure contemplates that the apparatuses described herein (e.g., apparatus shown in any one of FIGS. 1-9) can be used with systems or devices other than those provided as examples above.

Conventionally, the maxilla-mandibular occlusal relationship is positioned in a bite registration by the use of a traditional impression fork and gauge as described above. There are a number of such bite registration gauges available on the market including the GEORGE GAUGE. For example, the GEORGE GAUGE is described in U.S. Pat. No. 5,154,609 to George, issued Oct. 13, 1992, entitled "Instrument for registration of the dental bite." Conventional gauges typically consist of an impression fork for insertion into the patient's mouth and incorporate an upper incisor engagement portion and an extension protruding out of the patient's mouth. An independent lower incisor engagement portion is provided with an extension which is complementary to the upper extension, wherein a groove in the lower extension mates with the upper extension which slides freely therein. Protrusion and retrusion of the lower jaw with respect to the upper jaw causes a movement of the lower extension with respect to the upper extension. The positioning is typically anterior-posterior though commercial gauges exist that allow for three dimensional positioning. Calibrations are provided for measuring the relative movement there between and the exact scales and zero positions vary among the different gauges. Generally, a lock is provided between the extensions to hold the extensions at a given calibration for registering the bite at that calibration. The use of such conventional gauges to position and stabilize the mandible is not feasible for digital scanning of the bite as the device and/or impression material interfere by partially or fully obscuring the area required to be captured by the scan. The interference may be apparent to the user, or may only be apparent during the analysis of the captured scan.

Recently, new methods for digitally capturing of the open bite have been attempted however each has factors that prevent them from capturing an accurate scan or from being easy to use. Methods that involve capturing the bite with only the incisors embedded within the impression material to hold the positioning of the upper and lower mandible while leaving the remaining dentition exposed risk producing a cantilever effect and compression of retrodiscal tissue in the temporomandibular joint. The ability to hold the desired vertical positioning is also compromised. An alternative method of physically portioning a full impression fork is described in Charkhandeh et al. "A Fully Digital Workflow and Device Manufacturing for Mandibular Repositioning Devices for the Treatment of Obstructive Sleep Apnea; A Feasibility Study," Journal of Dental Sleep Medicine. 2017; 4(4):97-102. This alternative method is complicated, requires manually subdividing the impression fork, and will be difficult to adopt into an efficient work flow. Further, U.S. Patent Application Publication No. 2016/0008107 to Brunner, published Jan. 14, 2016, entitled "Bite fork with recesses" describes a device that allows for recesses on the contact surface between the bite fork and teeth for partial visualization of the tooth surfaces for better detection by an intraoral scanner, however the base of the impression fork remains positioned along the buccal portion of the occlusal contacting surface, and can be seen in the occlusal plane and compromises the quality of the impression.

Figure 2:
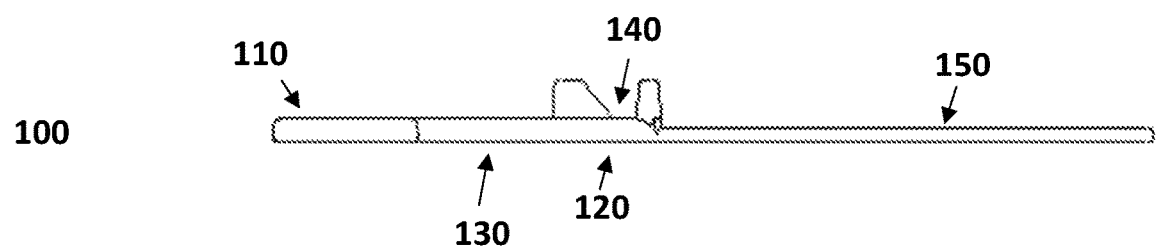
FIG. 2 is a diagram illustrating a side view of the apparatus shown in FIG. 1.
Figure 3:
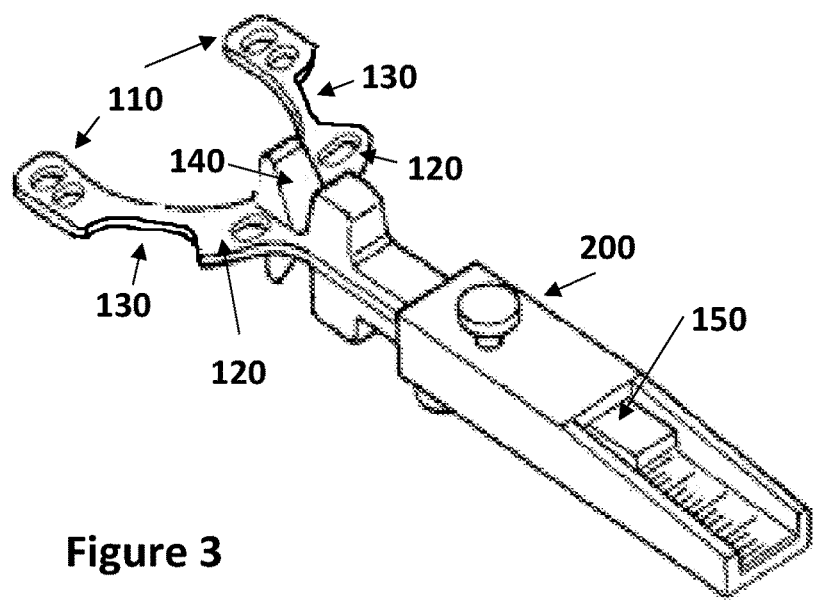
FIG. 3 is a diagram illustrating a perspective view of the apparatus shown in FIG. 1 connected to a George Gauge.
Figure 4:
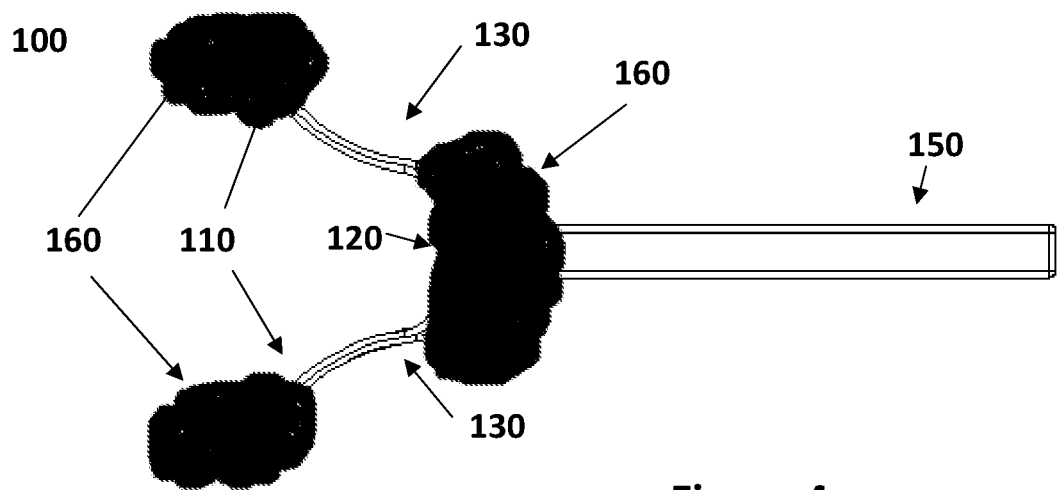
FIG. 4 is a top view of the apparatus shown in FIG. 1 with impression material provided on the molar and incisor pads.
Figure 5:
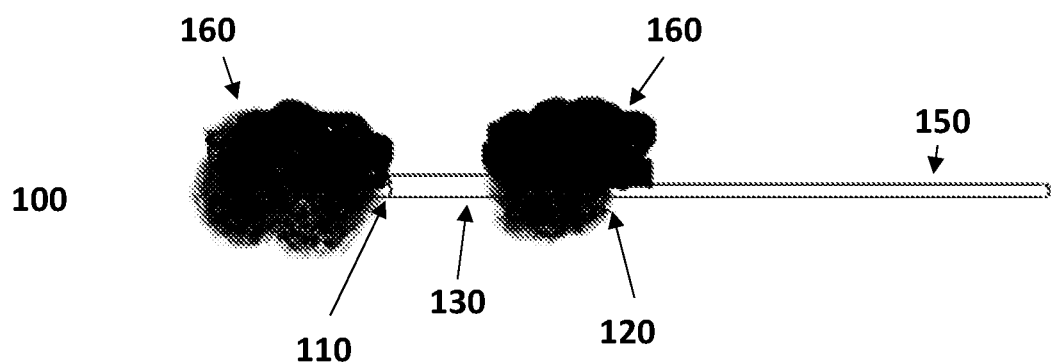
FIG. 5 is a side view of the apparatus shown in FIG. 4.

Referring now to FIGS. 1-5, an apparatus for use in obtaining digital open bite registration is shown. The apparatus can include a bite fork 100 configured to fit in a subject's mouth. The bite fork 100 can include at least one molar pad 110 and at least one incisor pad 120, each of the at least one molar pad 110 and the at least one incisor pad 120 having respective upper and lower bite surfaces. In FIGS. 1-5, the apparatus includes two molar pads 110 (e.g., left and right molar pads) and two incisor pads 120 (e.g., left and right incisor pads). The molar pad 110 and incisor pad 120 can be positioned in the occlusal plane, between the contact or masticatory surfaces of the subject's teeth, when the apparatus is inserted into the oral cavity (e.g., mouth). The apparatus can further include a lingual band 130 extending between the at least one molar pad 110 and the at least one incisor pad 120. Optionally, the lingual band 130 does not include bite surfaces. The lingual band 130 is instead used to link the at least one molar pad 110 and the at least one incisor pad 120. Optionally, the lingual band 130 includes bite surfaces that do not interfere with the focal point of the digital scanner (e.g., the buccal and/or facial contours of the dentition are not obscured by the lingual band). The apparatus can further include an incisal notch 140 configured to receive the subject's upper or lower incisors. For example, as shown in FIGS. 1-3, the incisal notch 140 is arranged on an upper bite surface of the incisor pad 120 and receives the subject's upper central incisors. Additionally, as shown in FIGS. 4 and 5, the apparatus can also include impression material 160 attached to one or more of the bite surfaces of the at least one molar pad 110 or the at least one incisor pad 120. In FIGS. 4 and 5, the impression material 160 is provided both the upper and lower bite surface of the at least one molar pad 110 and the at least one incisor pad 120. It should be understood that FIGS. 4 and 5 are provided only as an example and that impression material can optionally be provided on only a lower bite surface or an upper bite surface.

Figure 6:
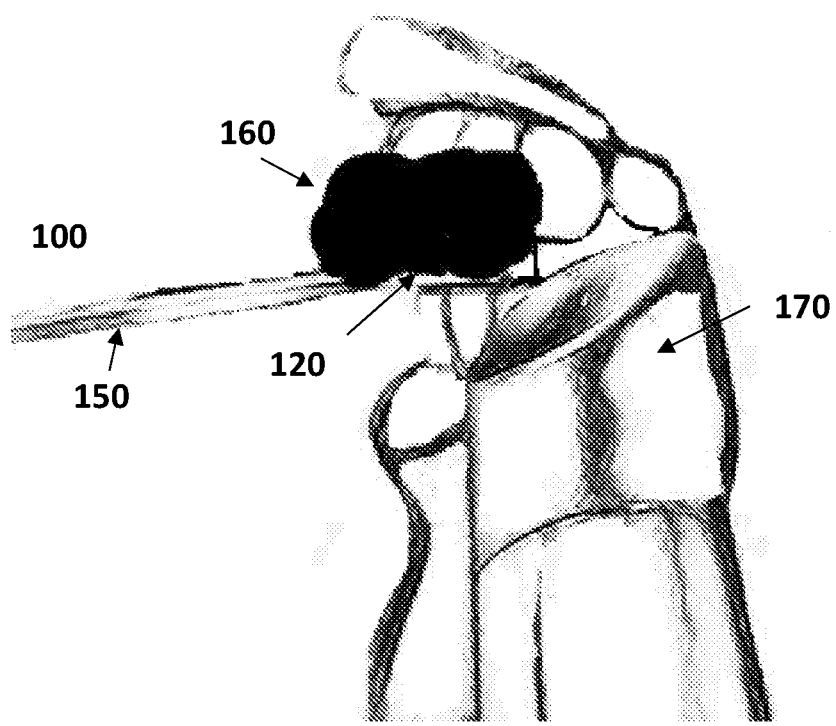
FIG. 6 is a diagram illustrating the apparatus shown in FIGS. 4 and 5 when inserted into the subject's mouth.

The bite fork 100 allows both the incisors and the molar regions to be embedded within the impression material 160, while providing a window that fully exposes the dentition. The window is created by connecting the molar pad 110 and the incisor pad 120 with the lingual band 130. As described below, the lingual band 130 is designed to remain out of the focal point of the digital scanner. In some implementations, the lingual band 130 is configured to extend proximate to a lingual portion of the subject's teeth. It should be understood that lingual is the side of the subject's teeth in the direction towards the tongue. Lingual is opposite to buccal or facial, which is the side of the subject's teeth in the direction towards the cheek or lip, respectively. Optionally, the lingual band 130 is configured to be restricted to a region proximate to the lingual portion of the subject's teeth. In some implementations, the lingual band 130 can contact occlusal contacting surfaces of the subject's teeth when inserted in the subject's oral cavity (e.g., the mouth). In other implementations, the lingual band 130 does not contact occlusal contacting surfaces of the subject's teeth when inserted in the mouth. The lingual portion 130 can therefore be configured such that it does not interfere with the buccal and/or facial portion of the subject's teeth. In some implementations, the lingual band 130 can be positioned away from the lingual edge of the subject's teeth, such that it is positioned more central, or directly central from the lingual edge. In all cases, the connection between the incisor pad 120 and the molar pad 110 is positioned such that it does not occlude the buccal and/or facial aspects of the dentition and such that the connection is out of the focal point of the digital scanner. Thus, the design of the window allows the full contour and detail of the buccal and/or facial surface of the dentition, including the portion of the dentition along the occlusal contacting surfaces to be captured without the interference from the apparatus. FIG. 6 provides an illustration of the bite fork 100 when inserted into the subject's mouth. As shown in FIG. 6, the subject bites the incisor pad 120, which has impression material 160 arranged on its upper bite surface. An intraoral digital scanner 170 can capture an image of the buccal and/or facial surfaces of the subject's teeth without interference because the lingual band (not visible), which connects the incisor pad 120 and the molar pad (not shown), is arranged in a region proximate to the lingual portion of the subject's teeth, e.g., behind the subject's teeth near the tongue in the view shown in FIG. 6. For example, CEREC OMNICAM digital scanner from DENSPLY SIRONA of York, Pa. or iTERO intraoral scanner from ALIGN TECHNOLOGY, INC. of San Jose, Calif. are example digital scanners. It should be understood that the iTERO and CEREC OMNICAM intraoral scanners are provided only as an example and that other scanners can be used with the techniques described herein. It should be noted that a portion 150 extends outside the subject's mouth, and this portion can be used to connect the bite fork 100 to another device such as a George Gauge or mandibular displacement device as described herein.

Referring again to FIGS. 1-5, the bite fork 100 is designed to stabilize the bite at the protruded position while enabling an unobstructed scan of the "maxillo-mandibular" relation. The bite fork 100 can be used on either the subject's upper or the lower teeth. For example, as shown in FIGS. 1-5, the bite fork 100 includes at least one molar pad 110 and at least one incisor pad 120, each having respective upper and lower bite surfaces. Impression material 160 can be arranged on one or more bite surfaces of the molar and/or incisor pads 110, 120 to engage with the subject's upper and/or lower teeth. Additionally, in FIGS. 1-3, the incisor notch 140 is provided to receive and engage with the subject's upper central incisors. In other words, in FIGS. 1-6, the bite fork 100 is used on the subject's maxilla or with the subject's upper teeth. The bite fork 100 shown in FIGS. 1-5 can be configured to engage with a segment that interacts with the other set of the subject's teeth (the subject's lower teeth in the example of FIGS. 1-6). The other segment can include a notch configured to receive the subject's lower central incisors. For example, this disclosure contemplates that the bite fork 100 shown in FIGS. 1-5 can be used with the George Gauge device described in U.S. Pat. No. 5,154,609 or other similar device that allows the precise positioning of the bite, upper arch relative to the lower arch. This is shown in FIG. 3, where the bite fork 100 is attached to a George Gauge 200. In particular, the bite fork 100 shown in FIGS. 1-5 can include a portion 150 extending outside of the subject's mouth and configured to engage (e.g., using a channel, groove, rail, etc.) such that it slides relative to the other segment. The bite fork 100 shown in FIGS. 1-5 and the other segment (e.g., the George Gauge 200 shown in FIG. 3) can be locked (e.g. using a clamp). The George Gauge is only one example device to which the bite fork 100 can be attached. Examples of other devices, including but not limited to those used for oral appliance therapy, with which the bite fork 100 can be used are provided above. It should be understood that the bite fork 100 shown in FIGS. 1-5 configured for use on the subject's upper teeth is provided only as an example. In another implementation, the incisor notch can be provided to receive and engage with the subject's lower central incisors such that the bite fork 100 can be used on the subject's mandible or with the subject's lower teeth.

This stabilization method was used to minimize the amount of distortion and inaccuracies in the bite registration by minimizing the possible cantilever effect and compression of retrodiscal tissue in the temporomandibular joint when no posterior support is present or movement of the mandible with respect to maxilla. This helps the position to maintain the desired vertical positioning of the bite.

The bite fork 100 can have a shape that fits to the arch of the teeth with bite surfaces at the incisor and molar positions (e.g., molar and incisor pads 110, 120 shown in FIGS. 1-5). The bite fork 100 can be configured such that the bite surfaces fit within the occlusal contacting surfaces in the incisor and molar positions (for example, a flat plate). Optionally, in some implementations, the apparatus can include one or more dental trays as described below with regard to FIG. 9. In these implementations, the molar pad 110 and/or incisor pad 120 are arranged on a tray. The tray has portions that extend up the surfaces of the subject's teeth, for example on the buccal, facial, and/or lingual surfaces and assist in receiving the subject's teeth. The bite surfaces are connected with a linkage (e.g., lingual band 130) that sits within the lingual space so as not to affect the digital scan capture of the dentition, in particular the contours of the buccal and/or facial aspects of the dentition. The linkage can also have a portion that extends up the surfaces of the subject's teeth along the lingual surface. As described above, the linkage can optionally extend into the occlusal contacting surface on the lingual side, however the linkage does not extend to the buccal and/or facial aspects of the contacting surface, and the linkage does not have a portion that extends up the buccal and/or facial aspect of the contacting surface.

Referring again to FIGS. 1-5, the bite fork 100 can be a "U" shaped arch or it can be one sided, for example either the left or right side. Alternatively, the bite fork linkage (e.g., the lingual band 130 shown in FIGS. 1-5) can take any shape that prevents it from interfering with the contours of the buccal and/or facial aspects of the dentition. This may take the form of a "V" shaped with straight linkages, or linkages that are curved and which meet in the center. It should be understood that when the linkages are curved (e.g., as opposed to "V" shaped), the linkages may be more flexible and/or not proximal to the subject's teeth. Design, shape, and/or material characteristics of the linkages can be selected depending on the application. To fit different arch shapes, the bite fork 100 can be made in different sizes, or it can be made of formable material such that the shape can be modified to suit the individual patient's arch. The material can be heat formable. The bite fork 100 provides a bite pad at the incisor or molar position, e.g., the incisor and molar pads 120, 110 shown in FIGS. 1-5. Impression material (e.g., impression material 160 as shown in FIGS. 4 and 5) can be attached to one or more bite surfaces of the molar pad 110 and/or the incisor pad 120. Generally, the incisor pad 120 is used to stabilize the position of the bite and achieve the desired three-dimensional (3D) positioning, including anterior-posterior positioning and vertical opening. The molar pad 110 is used to stabilize the temporomandibular joint and prevents it from any unwanted compression or intracapsular movement which could result in an inaccurate bite registration and distortion. The lingual band 130 may follow the lingual arch of the teeth.

The thickness of the bite pads (e.g., molar and incisor pads 110, 120 shown in FIGS. 1-5) can be selected to open the bite by an intended amount of vertical positioning and can be different at each of the positions. For example, the thickness can be greater at the incisors than at the molars. Alternatively, additional material in the form of pads or layers can be added to change the thickness of either of the surfaces and adjust the intended vertical position. These bite pads can be locked into place by design or attached with the use of the impression material. The relative lengths of the molar pad 110, the incisor pad 120 and the lingual band 130 is designed to allow enough space for scanning with no material in between the teeth. For example, the distance between the molar pad 110 and the incisor pad 120 is at least 10 mm. For example, in some implementations, the distance between the molar pad 110 and the incisor pad 120 can be about 20-30 mm.

At least one of the pads, either the incisor pad 120 or molar pad 110, can stabilize the bite during the scan. This is performed by providing a material that forms tightly to the surface of the teeth. For example, an impression material (e.g., impression material 160 as shown in FIGS. 4 and 5) can be attached to the molar pad 110 and/or the incisor pad 120. The impression material can be attached on the upper and/or lower bite surfaces of the molar pad 110 and/or incisor pad 120. The impression material can be dental impression material or some form of deformable material including, but not limited to, boil and bite thermoplastics. The engagement of the teeth to stabilize the bite can be either at the incisor pad 120 or the molar pad 110, or both the molar and incisor pads 110, 120. Optionally, the bite surface(s) of the molar pad 110 and/or the incisor pad 120 can include holes or other features such as ridges to help retain the impression material. As shown in FIGS. 1 and 3, the bite surfaces of the molar pad 110 and the incisor pad 120 includes a plurality of holes. Alternatively, the impression material can be provided previously mounted to the contacting surfaces of the device and then prepared, such as for example with a boil and bite thermoplastic.

To assist in accurately positioning the teeth in the correct position on the bite fork 100, the apparatus can include an "incisal notch" section. An example incisal notch 140 is shown in FIGS. 1-3. When placed in the incisal notch 140, the incisors (e.g., upper central incisors) are at a known position on the bite fork 100. This can help to locate the incisors such that a scale reading will correspond to a known position on the bite fork 100. For example, with the incisors properly centered within the incisal notch 140, the bite fork 100 can be used to position the incisors at a zero position on an associated scale. The incisal notch 140 can also help to position the incisors at different vertical opening measurements. For example, at 2 mm, 4 mm or 6 mm of incisor opening. It should be understood that the amount of incisor opening described above are provided only as examples and can be other amounts. To the right and left of the incisal notch 140, there is the anterior pad (e.g., incisor pad 120 shown in FIGS. 1-3) to help retain the bite registration material and allow enough inter-locking of the teeth to provide a stable "bite".

Figure 7:
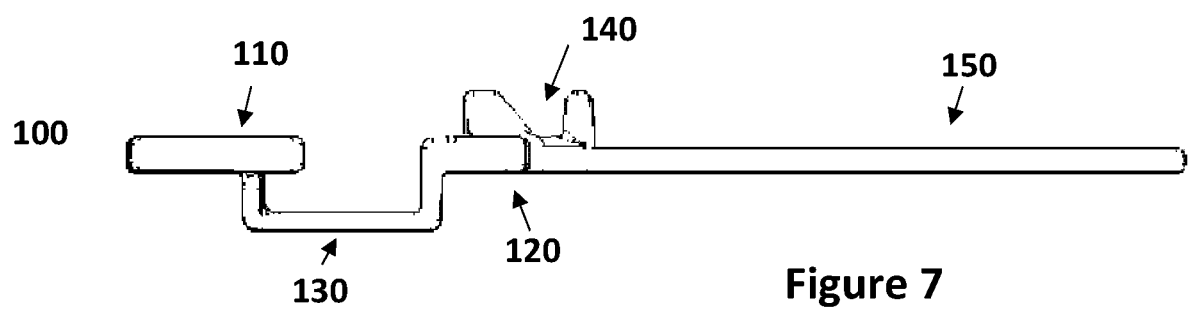
FIG. 7 is a diagram illustrating a side view of another example apparatus for use in obtaining digital bite registration according to implementations described herein.
Figure 8:
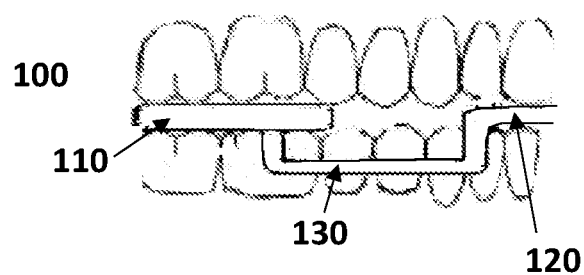
FIG. 8 is a side view of the apparatus shown in FIG. 7 when inserted into the subject's mouth.

Posterior to the incisor pad 120, there is a lingual band 130. If the bite fork 100 is a full arch design, there is a lingual band on each side as shown in FIGS. 1, 3, and 5. In other words, a respective lingual band 130 can extend between at least one incisor pad 120 and a left molar pad 110 and a right molar pad 110. This disclosure contemplates that the incisor pad can be a plurality of incisor pad, e.g., a left incisor pad and a right incisor pad. This design is shown in FIGS. 1-5. The purpose of the lingual band(s) is to maintain the bite fork's integrity and connecting the molar pad(s) and the incisor pad(s), while staying out of the digital scanner's focal point. This will allow the clinician (e.g., dentist) to scan the upper/lower relation without having to segment the bite and having to remove any material. The lingual band 130 can also help in capturing the scans as it can be configured to retract the tongue, which can otherwise come in between the teeth and make the scanning process more difficult. In some implementations, as shown in FIGS. 7 and 8, the lingual band 130 can be shaped to extend towards the gingival edge. The bite fork 100 shown in FIGS. 7 and 8 includes molar and incisor pads 110, 120 connected by the lingual band 130 and also includes the incisal notch 140, as well as the portion 150 that extends outside of the subject's mouth. In FIGS. 7 and 8, for example, the lingual band 130 can optionally be located caudally within the occlusal plane such that it is dropped on the lingual surface of the lower molars. The lingual band 130 can be offset caudally with respect to a plane of the occlusal contacting surfaces of the subject's teeth. FIG. 8 shows how the bite fork 100 appears from the lingual side of the subject's teeth. This design can further hide the lingual band 130 and can further retract the tongue. Optionally, in other implementations, the lingual band 130 can be located cranially within the occlusal plane. Although this design helps with capturing the digital scan, it is less helpful with retracting the subject's tongue.

To use the apparatus, a clinician (e.g., dentist) can first choose the desired "vertical" opening based on the clinical exam and then select the appropriate bite fork (e.g., apparatus shown in any one of FIGS. 1-9) and/or or impression material (e.g., pads) based on the desired vertical opening (e.g. 2 mm, 4 mm, 6 mm, etc.). The bite fork is then engaged with a segment that interacts with the other set of the subject's teeth. For example, if the bite fork is selected for the maxilla (upper teeth), the bite fork is engaged with a second segment that engages the lower teeth, and to which the bite fork can be positioned and engaged. The bite fork and segment can form a gauge similar to the George Gauge. Once the two segments are engaged, the desired protrusive position is selected (e.g. lower incisors relative to the upper incisors) and the bite fork position is set (e.g. +2 or −3 on the gauge). The bite fork is positioned in the patient's mouth to check for proper positioning and clearance. The bite fork is removed and impression material is added to either one or both of the incisor and molar pad (e.g., molar and/or incisor pads 110, 120 in any one of FIGS. 1-9), unless a boil and bite approach is used. The patient is instructed to close into the pre-set position. The material is allowed to set and any unwanted material is removed. The clinician checks for accuracy of the bite position. The digital bite registration scan is started as usual: a. Left bite: position the scanner beside the teeth and capture the image of the part with material in between the teeth (e.g., the lingual band area); and b. repeat with the right bite. The bite fork can be retained for a proper reference check if required. Alternatively, the bite fork may have been previously used to gather test data of the patient in a particular bite position. In this use, the desired position from the test data is maintained and the digital scan is captured.

Figure 9:
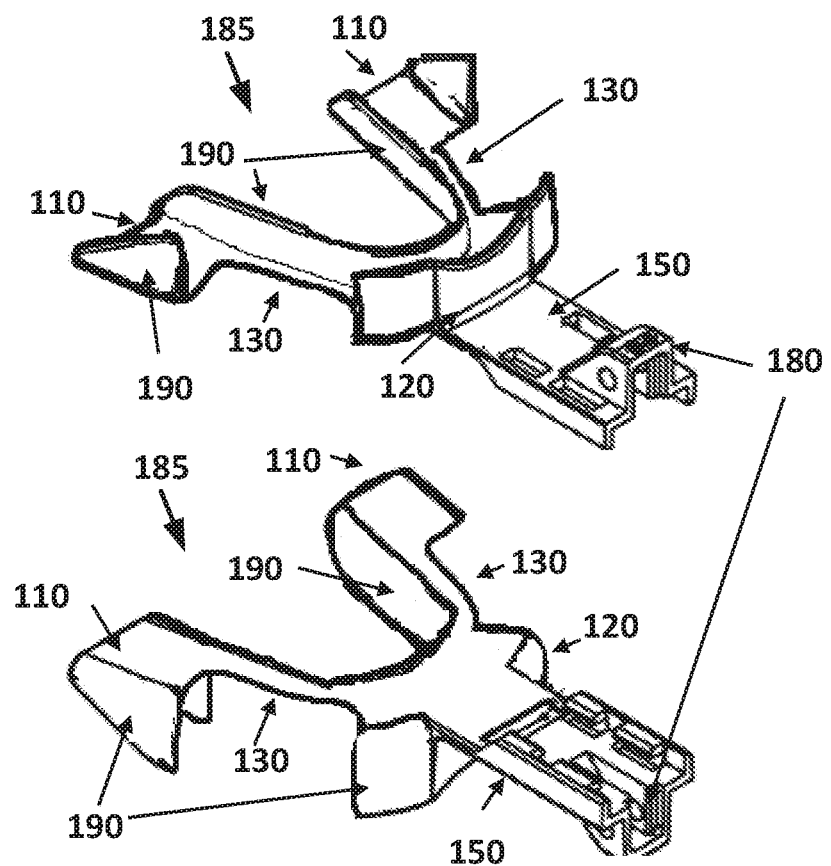
FIG. 9 is a diagram illustrating a perspective view of another example apparatus for use in obtaining digital bite registration according to implementations described herein.

Referring now to FIG. 9, another apparatus for use in obtaining digital open bite registration is shown. Unlike the apparatus shown in FIGS. 1-8, the apparatus shown in FIG. 9 includes dental trays 185. As shown in FIG. 9, the apparatus can include upper and lower dental trays, which can be connected to each other at respective portions 150 of the apparatus that extend outside of the subject's mouth. Each of the upper and lower dental trays includes walls 190 that extend along surfaces of the subject's teeth. As described below, the upper and lower dental trays are configured to receive the subject's teeth, and the walls 190 assist in receiving the subject's teeth. The portions 150 also include a connector 180, which is configured to attach to an external device such as a mandibular displacement devices (including those used to perform a sleep test or titration for oral appliance therapy) as discussed above. Each of the upper and lower dental trays can include molar pad(s) 110 having a bite surface and incisor pad(s) 120 having a bite surface. In FIG. 9, the upper dental tray includes left and right molar pads 110 and left and right incisor pads 120 (with upper bite surfaces), and the lower dental tray includes left and right molar pads 110 and left and right incisor pads 120 (with lower bite surfaces). Optionally, one or more of the bite surfaces can have impression material attached thereto as described herein.

The upper dental tray can include at least one upper molar tray and at least one upper incisor tray, and the lower dental tray can include at least one lower molar tray and at least one lower incisor tray. The spaces between the upper/lower molar tray and upper/lower incisor tray provide windows for exposing the subject's teeth and facilitate the ability to capture contours of buccal and/or facial dentition with a digital scanner. As shown in FIG. 9, an upper molar tray can receive at least one of the subject's upper molars, and a lower molar tray can receive at least one of the subject's lower molars. Additionally, the upper and lower molar pads 110 can be arranged on the upper and lower molar trays, respectively. Additionally, and as shown in FIG. 9, an upper incisor tray can receive at least one of the subject's upper incisors, and a lower incisor tray can receive at least one of the subject's lower incisors. Additionally, the upper and lower incisor pads 120 can be arranged on the upper and lower incisor trays, respectively. As shown in FIG. 9, respective lingual bands 130 connect a molar pad 110 and an incisor pad 120.

Methods

The apparatus described above with regard to FIGS. 1-9 can be used to obtain digital open bite registration. For example, the apparatus can be placed in a subject's mouth, and a digital image of the subject's open bite can be captured using a digital scanner with the apparatus in the subject's mouth. Thereafter, the digital image can be used to register a position of the subject's mandible relative to the subject's maxilla.

Optionally, in some implementations, the apparatus described above with regard to FIGS. 1-9 can be attached to a mandibular displacement device used to conduct a sleep test or a titration for oral appliance therapy. The sleep test or titration can then be conducted using the mandibular displacement device. Following performance of the sleep test or titration, the apparatus described above with regard to FIGS. 1-9 can also be used to obtain digital open bite registration. In other words, the apparatus described above with regard to FIGS. 1-9 can be used for both the sleep test or titration and bite registration.

EXAMPLES

Sixty-two individuals (41 males, 21 females) with obstructive sleep apnea were fitted for a custom oral appliance using a workflow that included the use of a Digital Bite Fork such as the apparatus described herein with regard to any one of FIGS. 1-9. The individuals ranged in age from 28 to 70 years and in BMI from 19.8 to 41.4 kg/m$^2$. The apnea-hypopnea index (AHI) of the individuals ranged from 7.8 to 101.8 events/h, with an average of 28.4 events/h. The individuals' full and protrusive ranges of motion ranged from 6.5 to 17.0 mm and 4.5 to 14.5 mm, respectively. All individuals were required to have adequate dentition for a custom oral appliance, which was defined as a minimum of 10 upper and 10 lower teeth and the absence of loose teeth, faulty restorations, and advanced periodontal disease. However, dental characteristics such as mild temporomandibular joint disorder, missing posterior teeth, severely misaligned teeth, anterior crowding of teeth, or narrow mandibular or maxillary arches, among others, did not preclude individuals from having a custom oral appliance fabricated.

A digital bite scan was performed using the Digital Bite Fork. The Digital Bite Fork was placed into a standard gauge at the individual's intended bite position, and a standard dental impression material was applied to the molar and incisal pads of the bite fork. The individual was instructed on how to bite into the fork by the dentist. Following preparation of the bite fork, the fork was placed into the individual's mouth and a digital scan was completed in a commercial intraoral scanner.

The bite positions ranged from 35 to 100% of the individual's protrusive range of motion. In all sixty-two cases, the dentist was able to take the bite using the Digital Bite Fork set at intended position. Preparation of the bite fork was generally completed in less than five minutes. In sixty-one cases, a digital scan was completed with the bite fork in place using an intraoral scanner. The intraoral bite scan took an average of 12 minutes. One individual could not have a digital bite scan completed due to missing teeth that prevented the intraoral scanning device from properly registering the teeth. In this individual, the bite was taken using a standard George gauge and a physical impression.

Custom oral appliances were fabricated based on a digital dentition scan and the digital bite scan completed with use of the bite fork. The protrusive levels of the custom oral appliances were verified using stone models and were found to be correct in all cases. Adjustments to the oral appliances were made as required to the appliance's bite or fit. A lack of adjustment to the bite indicated an accurate digital bite scan, and a lack of adjustment to the fit indicated an adequate dentition scan. Of the sixty-one appliances fabricated using the Digital Bite Fork, 37 (60.6%) required no adjustments to the bite or fit. Twenty (32.8%) required minor adjustments to the fit, usually to reduce discomfort of the appliance due to tightness on a particular tooth. Adjustments to fit were performed at the discretion of the dentist and were based on feedback from the individual. Therefore, it is likely that more appliances than necessary were adjusted for fit. Three appliances (4.9%) had adjustments made to the bite, and one appliance (1.6%) was fabricated incorrectly (lab error) and had to be completely remade. The replacement appliance did not require any adjustments.

In summary, data from a cohort of 62 individuals showed that the Digital Bite Fork can be used to effectively scan an individual's bite position for fabrication of a custom oral appliance. The custom appliances made from a digital workflow that includes the Digital Bite Fork generally fit well and do not require adjustment.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An apparatus for use in obtaining digital open bite registration, comprising:
   a bite fork configured to fit in a subject's mouth, wherein the bite fork comprises at least one molar pad and at least one incisor pad, each of the at least one molar pad and the at least one incisor pad having respective upper and lower bite surfaces; and
   a lingual band extending between the at least one molar pad and the at least one incisor pad, wherein the bite fork has a shape that fits a dental arch of the subject, each of the bite fork and the lingual band having respective lingual and buccal sides, wherein the lingual and buccal sides of the bite fork are arranged on opposite sides of the dental arch, wherein the lingual band extends from each of the at least one molar pad and the at least one incisor pad such that the buccal side of the lingual band is recessed from the buccal side of the bite fork, wherein the lingual band is arranged on the lingual side of the bite fork, and wherein the lingual band is configured to not interfere with a buccal portion of the subject's teeth.

2. The apparatus of claim 1, wherein the lingual band is configured to extend proximate to a lingual portion of the subject's teeth.

3. The apparatus of claim 1, wherein the lingual band is configured to be restricted to a region that is proximate to a lingual portion of the subject's teeth.

4. The apparatus of claim 1, wherein the lingual band is coplanar with the at least one molar pad and the at least one incisor pad.

5. The apparatus of claim 1, wherein the lingual band is shaped to extend towards a gingival edge.

6. The apparatus of claim 1, wherein the lingual band is shaped to be offset caudally with respect to a plane of the occlusal contacting surfaces of the subject's teeth.

7. The apparatus of claim 6, wherein the lingual band offset is configured to extend below at least a portion of the subject's lower teeth.

8. The apparatus of claim 6, wherein the lingual band offset is about 5 to 8 mm relative to the bite fork.

9. The apparatus of claim 1, wherein the lingual band is positioned such that the lingual band is out of a focal point of a digital scanner when the bite fork is positioned in the subject's mouth.

10. The apparatus of claim 9, wherein the digital scanner is configured to capture a digital image of the subject's open bite, the digital image being used to register a position of the subject's mandible relative to the subject's maxilla.

11. The apparatus of claim 10, wherein the lingual band is configured to retract the subject's tongue.

12. The apparatus of claim 1, further comprising an incisal notch configured to receive the subject's upper incisors.

13. The apparatus of claim 12, wherein the incisal notch is configured to position the subject's upper and lower incisors with a variable amount of vertical opening there between.

14. The apparatus of claim 1, further comprising an impression material attached to at least one of the bite surfaces of the at least one molar pad or the at least one incisor pad.

15. The apparatus of claim 14, wherein a thickness of the impression material is selected to provide a predetermined amount of space between the subject's upper and lower teeth.

16. The apparatus of claim 15, wherein the impression material comprises one or more layers of impression material.

17. The apparatus of claim 1, further comprising at least two molar pads and a plurality of lingual bands, wherein each respective lingual band extends between the at least one incisor pad and one of the at least two molar pads.

18. The apparatus of claim 1, further comprising:
   an upper molar tray for receiving at least one of the subject's upper molars; and
   a lower molar tray for receiving at least one of the subject's lower molars, wherein the at least one molar pad comprises an upper molar pad having the upper bite surface and a lower molar pad having the lower bite surface, and wherein the upper molar pad is arranged on the upper molar tray and the lower molar pad is arranged on the lower molar tray.

19. The apparatus of claim 1, further comprising:
   an upper incisor tray for receiving at least one of the subject's upper incisors; and
   a lower incisor tray for receiving at least one of the subject's lower incisors, wherein the at least one incisor pad comprises an upper incisor pad having the upper bite surface and a lower incisor pad having the lower bite surface, and wherein the upper incisor pad is arranged on the upper incisor tray and the lower incisor pad is arranged on the lower incisor tray.

20. The apparatus of claim 1, wherein the bite fork further comprises a portion configured to extend outside of the subject's mouth.

21. The apparatus of claim 20, wherein the bite fork further comprises a connector arranged on the portion configured to extend outside of the subject's mouth, and wherein the connector is configured to be attachable to an external device.

22. The apparatus of claim 21, wherein the external device is a device for precisely positioning the subject's bite or a mandibular displacement device.

23. The apparatus of claim 1, wherein a lingual portion of the subject's teeth is on a side of the subject's teeth in a direction toward the subject's tongue.

24. The apparatus of claim 1, wherein the lingual band is configured to not extend to the buccal portion of the subject's teeth.

* * * * *